(12) United States Patent
Perot et al.

(10) Patent No.: US 11,376,373 B2
(45) Date of Patent: Jul. 5, 2022

(54) MEDICAL DEVICE FOR INJECTING A COMPOSITION PROVIDED WITH A SAFETY NEEDLE COVER

(71) Applicant: Becton Dickinson France, Le Pont de Claix (FR)

(72) Inventors: Frédéric Perot, Saint Paul de Varces (FR); Michaël Fiard, Grenoble (FR); Gilles Bernede, Arbusigny (FR)

(73) Assignee: Becton Dickinson France, Le Pont de Claix (FR)

( * ) Notice: Subject to any disclaimer, the term of this patent is extended or adjusted under 35 U.S.C. 154(b) by 18 days.

(21) Appl. No.: 16/970,041

(22) PCT Filed: Feb. 13, 2019

(86) PCT No.: PCT/EP2019/053483
§ 371 (c)(1),
(2) Date: Aug. 14, 2020

(87) PCT Pub. No.: WO2019/158549
PCT Pub. Date: Aug. 22, 2019

(65) Prior Publication Data
US 2021/0093799 A1 Apr. 1, 2021

(30) Foreign Application Priority Data
Feb. 16, 2018 (EP) ..................................... 18305167

(51) Int. Cl.
*A61M 5/32* (2006.01)
(52) U.S. Cl.
CPC ... *A61M 5/3271* (2013.01); *A61M 2005/3247* (2013.01); *A61M 2005/3267* (2013.01)

(58) Field of Classification Search
CPC .. A61M 5/3271; A61M 5/321; A61M 5/3272; A61M 5/326; A61M 5/321571;
(Continued)

(56) References Cited

U.S. PATENT DOCUMENTS 9,192,731 B2  11/2015  Roberts et al.
9,314,574 B2   4/2016  Roberts et al.
(Continued)

FOREIGN PATENT DOCUMENTS

CN   204395141 U   6/2015
CN   107261263 A  10/2017
(Continued)

*Primary Examiner* — Bhisma Mehta
*Assistant Examiner* — Phoebe Anne Staton
(74) *Attorney, Agent, or Firm* — The Webb Law Firm

(57) ABSTRACT

A medical injection device for supporting a medical container, the medical container comprising a barrel adapted to contain a composition and a needle extending from a distal end of the barrel, wherein the medical injection device comprises: a body configured to receive at least a part of the medical container, a plunger axially movable relative to the body along an axis of the body, needle cover movable relative to the body along the axis, the needle cover being configured to move successively between storage position wherein the needle cover covers the needle, an injection position wherein the needle cover exposes at least partially the needle, a safety position wherein the needle cover covers the needle and is prevented from moving back to the injection position.

12 Claims, 12 Drawing Sheets

(58) Field of Classification Search
CPC ............ A61M 5/31571; A61M 5/3234; A61M 2005/3267; A61M 2005/3247; A61M 5/3243; A61M 2205/273; A61M 5/20; A61M 5/31501; A61M 5/3202; A61M 5/3204; A61M 2205/27; A61M 5/3213; A61M 2205/276; A61M 5/50; A61M 2005/2013; A61M 5/2003
See application file for complete search history.

(56) References Cited

U.S. PATENT DOCUMENTS

| | | |
|---|---|---|
| 9,694,138 B2 | 7/2017 | Ekman et al. |
| 9,962,497 B2 | 5/2018 | Takemoto |
| 10,022,505 B2 | 7/2018 | Hu |
| 10,449,305 B2 | 10/2019 | Aneas |
| 2011/0319833 A1 | 12/2011 | Chun |
| 2013/0204200 A1* | 8/2013 | Roberts ............... A61M 5/3257 604/198 |
| 2014/0303564 A1* | 10/2014 | Roberts ............... A61M 5/3271 604/198 |
| 2019/0240409 A1* | 8/2019 | Holmqvist .......... A61M 5/3271 |

FOREIGN PATENT DOCUMENTS

| | | |
|---|---|---|
| EP | 2588173 B1 | 10/2015 |
| RU | 2573793 C2 | 1/2016 |
| WO | 2012000832 A1 | 1/2012 |
| WO | 2012000833 A1 | 1/2012 |
| WO | 2016120185 A2 | 8/2016 |

* cited by examiner

MEDICAL DEVICE FOR INJECTING A COMPOSITION PROVIDED WITH A SAFETY NEEDLE COVER

CROSS-REFERENCE TO RELATED APPLICATIONS

This application is the U.S. national phase of International Application No. PCT/EP2019/053483 filed Feb. 13, 2019, and claims priority to European Patent Application No. 18305167.1 filed Feb. 16, 2018, the disclosures of which are hereby incorporated by reference in their entirety.

TECHNICAL FIELD OF THE INVENTION

The invention relates to a medical injection device for injecting a composition contained in a medical container, the device being provided with a safety needle cover.

TECHNICAL BACKGROUND

Prefilled injection devices are common containers to deliver drugs or vaccines to patients and include syringes, cartridges and autoinjectors or the like. They usually comprise a sealing stopper in gliding engagement into a container, the container being filled with a pharmaceutical composition in order to provide the practitioners with a ready-to-use injection device for patients.

A container comprises a barrel having a substantially cylindrical shape, and comprises a proximal end able to be stoppered by a sealing stopper, a distal end wherein the pharmaceutical composition is expelled from the container, and a lateral wall extending between the proximal end and the distal end. In practice, the sealing stopper is aimed at moving, upon the pressure exerted by a plunger rod, from a proximal end of the barrel towards the distal end of the barrel, thereby expelling the drug contained into the barrel.

When compared to empty injection devices that are filled with a vial-stored pharmaceutical composition just prior to the injection to the patient's body, the use of prefilled injection devices leads to several advantages. In particular, by limiting the preparation prior to the injection, the prefilled injection devices provide a reduction of medical dosing errors, a minimized risk of microbial contamination and an enhanced convenience of use for the practitioners. Furthermore, such prefilled containers may encourage and simplify self-administration by the patients which allows reducing the cost of therapy and increasing the patient adherence. Finally, prefilled injection devices reduce loss of valuable pharmaceutical composition that usually occurs when a pharmaceutical composition is transferred from a vial to a non-prefilled injection device. This results in a greater number of possible injections for a given manufacturing batch of pharmaceutical product thus reducing buying and supply chain costs.

The injection can be a self-injection or can be performed by a user, such as a health care professional, to another person. In both cases, in order to perform the injection, the user positions the device in the vicinity of the injection area of the body, and pricks the skin with the needle. The user then pushes the plunger rod to carry out the injection of the composition. At the end of the injection, the user withdraws the device from the skin of the body.

When using the injection device, in particular just before and after performing the injection, the needle is left free and unprotected. This represents a high risk of accident for the user as well as for the patient or any person around who were to come into contact with the needle, and may lead to severe injuries.

BRIEF DESCRIPTION OF THE INVENTION

The invention aims to provide an injection device for injecting a composition contained in a medical container, such as a syringe, which prevents the user, the patient, or any person around the device, to come into contact with the needle of the medical container during use of the device, especially just before and after performing the injection.

In that way, the needle is not physically accessible, and the risk of accidental pricks or wounds generally caused by contact of the needle with a person close to the device is nullified.

The invention aims also to provide an injection device that keeps the needle not physically accessible after an injection has been performed, thereby preventing any further injection to be performed.

Another object of the invention is to provide an injection device to help the patient to self-inject regularly with drugs.

Another aspect of the invention is to provide an injection device ensuring that the needle cover cannot be moved in safety position as long as the injection is not completed.

To that purpose, the invention provides a medical injection device for supporting a medical container, said medical container comprising a barrel adapted to contain a composition and a needle extending from a distal end of the barrel, wherein the medical injection device comprises:
  a body configured to receive at least a part of the medical container,
  a plunger axially movable relative to the body along an axis of the body, and
  a needle cover movable relative to the body along the axis, the needle cover being configured to move successively between a storage position wherein the needle cover covers the needle, an injection position wherein the needle cover exposes at least partially the needle, a safety position wherein the needle cover covers the needle and is prevented from moving back to the injection position,
  wherein the medical injection device further comprises:
  a groove comprising a first branch and a second branch extending from a junction with the first branch, and
  a lug connected to the needle cover, the needle cover being configured to move from the storage position to the injection position when the lug is in the first branch, the needle cover being configured to move from the injection position to the safety position when the lug is in the second branch.

Said medical injection device is characterized in that, when the needle cover is in the injection position, the plunger is configured to transition the lug from the first branch to the second branch when said plunger moves distally.

According to the invention, the needle cover may be locked in the safety position. In this case, the needle cover can only be locked in safety position once the full dose of drug has been injected. This injection device enables to prick the needle in different sites of the patient's body: each time, the needle cover is retracted in injection position and expanded in storage position again, without any risk to lock the needle cover in safety position.

In this application, the "distal direction" is to be understood as meaning the direction of injection, with respect to the medical container the device of the invention is to be mounted on. The distal direction corresponds to the travel direction of the plunger during the injection, the pharmaceutical composition contained initially in the medical container being expelled from said medical container. The "proximal direction" is to be understood as meaning the opposite direction to said direction of injection.

According to optional features of the invention, taken separately or in combination if technically appropriate:

the plunger is configured to rotate the groove when the plunger reaches a distal triggering position so that the lug moves from the first branch to the second branch;

the plunger comprises an inclined surface configured to cause the groove to rotate relative to the plunger;

the device further comprises a ring in rotatable engagement with the needle cover; the groove being positioned on the ring, the lug being positioned on the needle cover;

the lug is on a flexible arm, the plunger being configured to deflect the flexible arm when the plunger reaches a distal triggering position so that the lug moves from the first branch to the second branch;

the flexible arm extends proximally from the needle cover, the groove being positioned on the body;

the groove has a V-shape having a summit located proximally;

the device further comprises locking means configured to lock the needle cover in safety position;

the locking means comprise at least one flexible tab configured to be deflected when the needle cover moves from the injection position to the safety position, the flexible tab being configured to prevent proximal movement of the needle cover when the needle cover is in safety position;

the needle cover comprises a stop surface arranged so that the flexible tab abuts against the stop surface when the needle cover is in safety position;

the second branch is longer than the first branch;

the device further comprises a ring cooperating with the needle cover to prevent any axial movement of the plunger when the needle cover is in storage position, and to allow axial movement of the plunger in the distal direction to expel a pharmaceutical composition contained in the barrel from the needle when the needle cover is in injection position, wherein the ring comprises a locking member configured to form an abutment preventing any axial movement of the plunger in the distal direction when the needle cover is in storage position, and be moveable so that the plunger is allowed to move axially in the distal direction when the needle cover is in injection position;

the locking member is a flexible member configured to form an abutment preventing any axial movement of the plunger in the distal direction when the needle cover is in storage position, and be deflected inwardly so that the plunger is allowed to move axially in the distal direction when the needle cover is in injection position;

the flexible member comprises at least two flexible legs extending proximally from the ring and the needle cover comprises a locking ring cooperating with said legs such that, when the needle cover is in the storage position, the locking ring is located around a distal base of the legs and when the needle cover is moved to the injection position, the locking ring is caused to slide along the legs, thereby retracting each leg inwardly;

the locking member comprises legs, the ring being configured to rotate relative to the plunger between a locking position wherein the legs abut the plunger so that the plunger cannot move distally and an unlocking position wherein the legs do not abut the plunger so that the plunger can move distally;

the plunger comprises a central plunger rod configured to push a stopper in the medical container;

the plunger comprises an outer plunger body;

the outer plunger body is provided with a color indicator configured to be aligned with a window of the body at the end of injection in order to indicate to a user the end of injection.

Another object of the invention is to prevent injection as long as pricking as not been completed.

To that end, a medical injection device for supporting a medical container comprising a barrel and a needle extending from a distal end of the barrel is provided. Said medical injection device comprises:

a body configured to receive at least a part of the medical container, a plunger movable relative to the body along an axis of the body, a needle cover movable relative to the body along the axis, configured to move in a distal direction between a storage position wherein the needle cover covers the needle and an injection position wherein the needle cover exposes a tip of the needle, a ring cooperating with the needle cover to prevent any axial movement of the plunger when the needle cover is in storage position, and to allow axial movement of the plunger in the distal direction to expel a pharmaceutical composition contained in the barrel from the needle when the needle cover is in injection position, wherein the ring comprises a locking member configured to form an abutment preventing any axial movement of the plunger in the distal direction when the needle cover is in storage position, and be moved so that the plunger is allowed to move axially in the distal direction when the needle cover is in injection position.

Said device allows the user to carry out the injection of a pharmaceutical composition to a patient or himself, while preventing any person in the vicinity of the device, in particular the patient and himself, to contact the needle of the medical container off injection, thereby avoiding injuries and making the device safe. Indeed, in storage position, the needle cover covers the needle, thereby preventing any contact between the needle and any person around the device. In injection position, the needle is positioned into the skin of the patient, and the injection can be carried out.

According to other optional features of said device, taken separately or in combination when technically possible:

The needle cover is further configured to move in a proximal direction between the injection position wherein the needle cover exposes a tip of the needle, and a safety position wherein the needle cover covers the needle.

The locking member is configured to be deflected inwardly when the needle cover is in injection position so that the plunger is allowed to move axially in the distal direction when the needle cover is in injection position.

The locking member comprises at least two legs extending proximally from the ring.

According to one embodiment, the legs are flexible; by "flexible", we mean that the legs may be deflected by a force inferior to 20N.

The needle cover comprises a locking ring cooperating with said legs such that, when the needle cover is in the storage position, the locking ring is located around a distal base of the legs and when the needle cover is moved to the injection position, the locking ring is caused to slide along the legs, thereby retracting each leg inwardly. This embodiment provides a quite simple structure, which achieves an efficient axial blocking of the plunger when the needle cover is in storage position and an easy mechanical transition between the blocking/releasing states of the plunger.

The ring is preferably in rotatable engagement with the needle cover.

The locking member comprises legs, the ring being configured to rotate relative to the plunger between a locking position wherein the legs abut the plunger so that the plunger cannot move distally and an unlocking position wherein the legs do not abut the plunger so that the plunger can move distally.

According to one embodiment, the legs are rigid; by "rigid", we mean that the legs cannot be deflected by a force inferior to 20N.

The plunger comprises at least two arms. In locking position the legs of the ring are aligned with the arms of the plunger. In unlocking position, the legs of the ring are not aligned with the arms of the plunger.

The plunger comprises a triggering member configured to engage the ring when moving axially in the distal direction, thereby causing the ring to rotate from a first to a second position.

The ring and the plunger comprise respective inclined surfaces configured to cause the ring to rotate relative to the plunger when the plunger moves axially in the distal direction. Such inclined surfaces are quite simple to manufacture and simplify the overall structure of the device.

The ring is configured to allow the needle cover to be urged to a safety position that is more distal than the storage position when the ring is in the second position. In safety position, the needle cover covers the needle as in the storage position, but is located more distally compared to the storage position, which allows said needle cover to be blocked in such safety position as explained in more details in the following.

The needle cover or the ring comprises a lug engaging a groove of the ring or the needle cover, said groove comprising a first branch extending axially and a second branch extending obliquely relative to the first branch, the first and second branches being interconnected proximally.

The distal end of the second branch is located in a more distal position than the distal end of the first branch.

The lug and the groove are configured so that when the ring is in the first position, the lug engages the first branch of the groove and when the ring is in the second position, the lug engages the second branch of the groove. Hence, in safety position, the lug is located more distally compared to the storage position. As a consequence, the needle cover is located more distally compared to the storage position.

The ring comprises a retaining portion engaging the locking ring when the needle cover is in the safety position to maintain the needle cover in said safety position. The needle is covered by the needle cover, and remains covered due to the blocking of the needle cover in the safety position by the ring.

The plunger comprises a central plunger rod and an outer plunger body, the outer plunger body being configured to abut the free end of the flexible member when the needle cover is in the distal storage position and to move axially along the flexible member when the needle cover is in the injection position, thereby allowing the central plunger rod to push a stopper of the medical container in the distal direction. Such structure is particularly adapted for the plunger to abut the flexible member, as well as to achieve the two functions described previously, of both injecting the pharmaceutical composition and actuating the ring.

BRIEF DESCRIPTION OF THE DRAWINGS

Further features and advantages of the invention will become apparent from the detailed description to follow, with reference to the appended drawings, in which.

DETAILED DESCRIPTION OF EMBODIMENTS OF THE INVENTION

Figure 1:
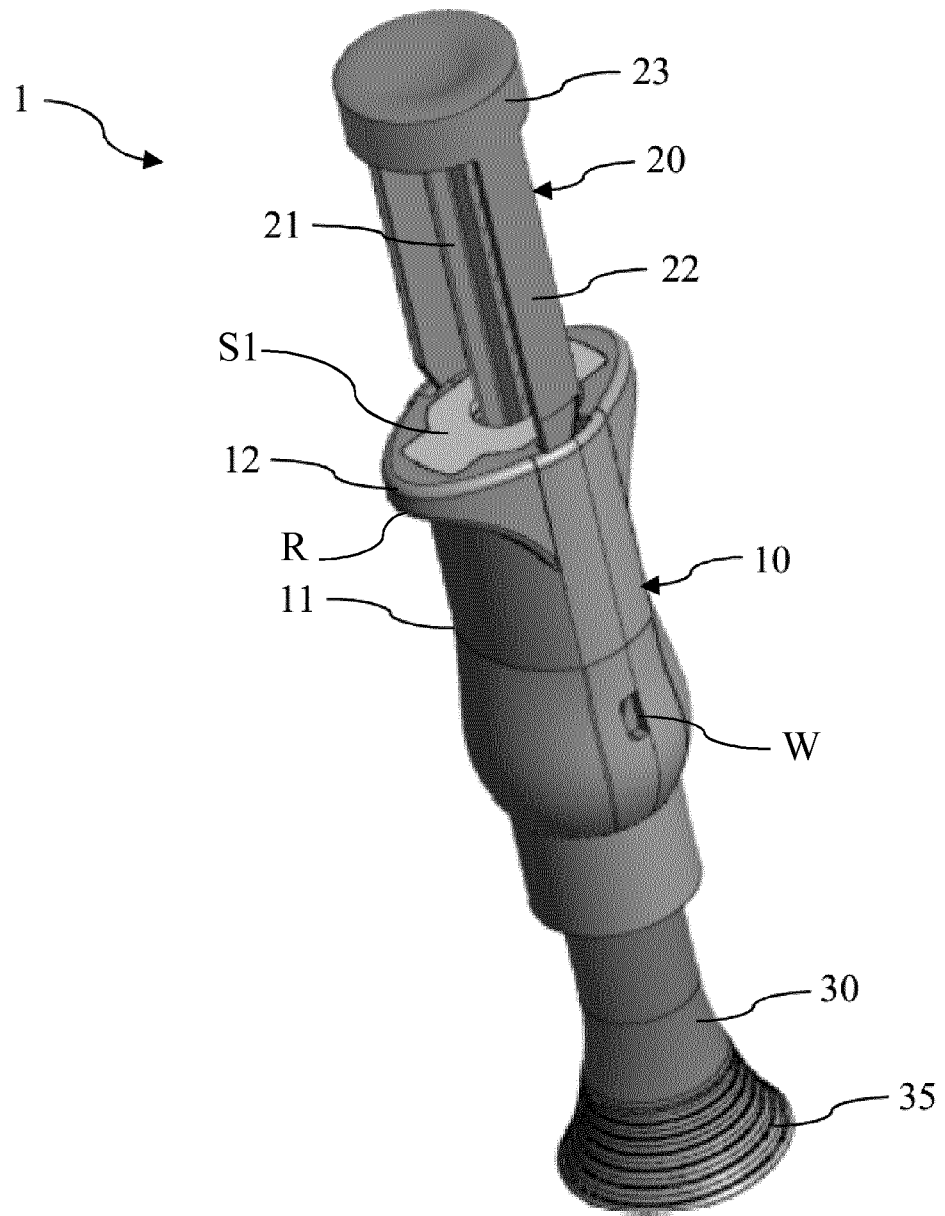
FIG. 1 is a perspective view of an embodiment of the medical injection device of the invention, before use, the needle cover being in the storage position.

The invention proposes a medical injection device for supporting a medical container.

Prior to the injection, the medical container is filled with a composition intended to be injected, and stoppered with a stopper inserted therein. The stoppered medical container is then mounted on the device, and the injection of the composition can be carried out.

An embodiment of the injection device is represented in FIGS. 1 to 11.

According to this embodiment, the injection device 1 comprises a body 10 extending along a longitudinal axis (A). The body 10 preferably has a cylindrical shape.

The body 10 is adapted to be held by a user's hand. To that end, the body 10 is provided with a grip surface 11 limited proximally by gripping means 12, such as arms or a flange for example, that extend radially outwardly from the axis (A). The flange may be provided with an inferior surface R pierced by a hole in order to ease assembling and disassembling of the injection device. When using the device 1, the user can easily grab the body so that the palm of his hand contacts the grip surface 11 and the upper end of his hand abuts the gripping means 12, thus facilitating the handling of the device. Alternatively, the user can hold the grip surface 11 between his index finger and his middle finger, both abutting the gripping means, as he would normally hold a standard syringe. The device is thus handheld and the dimensions and the weight of the device are advantageously adapted for this purpose.

The medical container 90 comprises a barrel 91 including a proximal end provided with a flange 92 and a distal end having a tip 93 and a needle 94 extending from thereon. Once mounted in the body 10, the medical container 90 is maintained fixed axially relative to said body. The medical container 90 is preferably a pre-filled syringe.

The device 1 comprises a plunger 20. The plunger extends along the axis (A). The plunger advantageously comprises a central plunger rod 21 and an outer plunger body 22 extending around and at a distance from the central plunger rod 21. The central plunger rod and outer plunger body are preferably connected to a proximal end 23 of the plunger. The plunger 20 is translationally movable relative to the body along the axis (A). In use, the central plunger rod 21 slides inside the medical container 90, in particular in a distal direction wherein said central plunger rod 21 pushes a stopper contained therein to expel the composition contained in a medical container 90 from the needle 94. The outer plunger body 22 may slide between the wall of the body 10 and the medical container 90. The outer plunger body 22 may comprise two arms 24. The outer plunger body could also comprise more than two arms. Each arm may be provided with an end member 26 that defines an inclined surface 27 at its distal end 25. Alternatively, the outer plunger body could comprise a cylindrical housing. The cylindrical housing may be provided with a frustoconical distal end or with a plurality of inclined legs.

The device 1 further comprises a needle cover 30. The needle cover preferably extends inside the body 10 and around the medical container 90. The needle cover is configured to act as a physical barrier between the needle 94 of the medical container 90 and the user or any person in the vicinity of the device, thereby avoiding any contact with the needle and preventing any possible injury. In that matter, the needle cover 30 is preferably made of a rigid material so that in the case where a person applies a pressure onto the needle cover towards the needle 94, the needle cover maintains its structural integrity and does not deform.

The needle cover 30 is translationally movable relative to the body 10 along the axis (A), in particular in the proximal direction between a storage position wherein the needle cover 30 covers the needle 94 and an injection position wherein the needle cover 30 exposes at least partially the needle 94. The needle cover 30 is biased in the distal direction by a spring member 80, having advantageously one end connected to the flange 92 of the medical container and another end connected to the needle cover 30.

The storage position corresponds to a position wherein the needle cover 30 covers the needle 94, including the tip 93, and acts as a physical barrier as explained before. The needle cover may be in such position before use of the device, that is to say, when the device is stored in an appropriate place or when carried from a place to another.

When the needle cover is in storage position, the spring 80 is preferably partially compressed. After use of the device, the needle cover 30 is urged in the distal direction from the injection position to a safety position wherein it covers the needle. Preferably, said safety position is more distal than the storage position. When the needle cover is in storage position, the spring 80 is preferably less compressed than when the needle cover is in injection position but more compressed than when the needle cover is in safety position. In the device illustrated in FIG. 1, the needle cover 30 is in the storage position. The needle 94 covered by the needle cover 30 is visible by transparency in FIG. 3. Here, the entirety of the needle 94 is covered by the needle cover 30 which protrudes proximally from the needle 94.

A cap 35 is optionally mounted on the distal end 33 of the needle cover 30 to ease the removal of the needle shield or of the rigid needle shield (not represented) covering the needle 94.

The injection position corresponds to a position wherein the needle cover 30 exposes at least partially the needle 94, thereby making the needle physically accessible, which makes possible the pricking of the skin of the patient and the subsequent injection of the pharmaceutical composition.

The device 1 may further comprise a ring 40 fixed axially relative to the body 10. The ring 40 is in rotatable engagement with the needle cover 30. The ring 40 comprises a locking member 42 configured to prevent any movement of the plunger as long as the needle cover is in storage position. When the needle cover 30 is in storage position, the outer plunger body 22 abuts against the locking member 42 of the ring 40, in order to prevent any movement of the plunger in distal direction. When the needle cover 30 is in injection position, the outer plunger body does not abut anymore against the locking member 42 of the ring 40.

Figure 2:
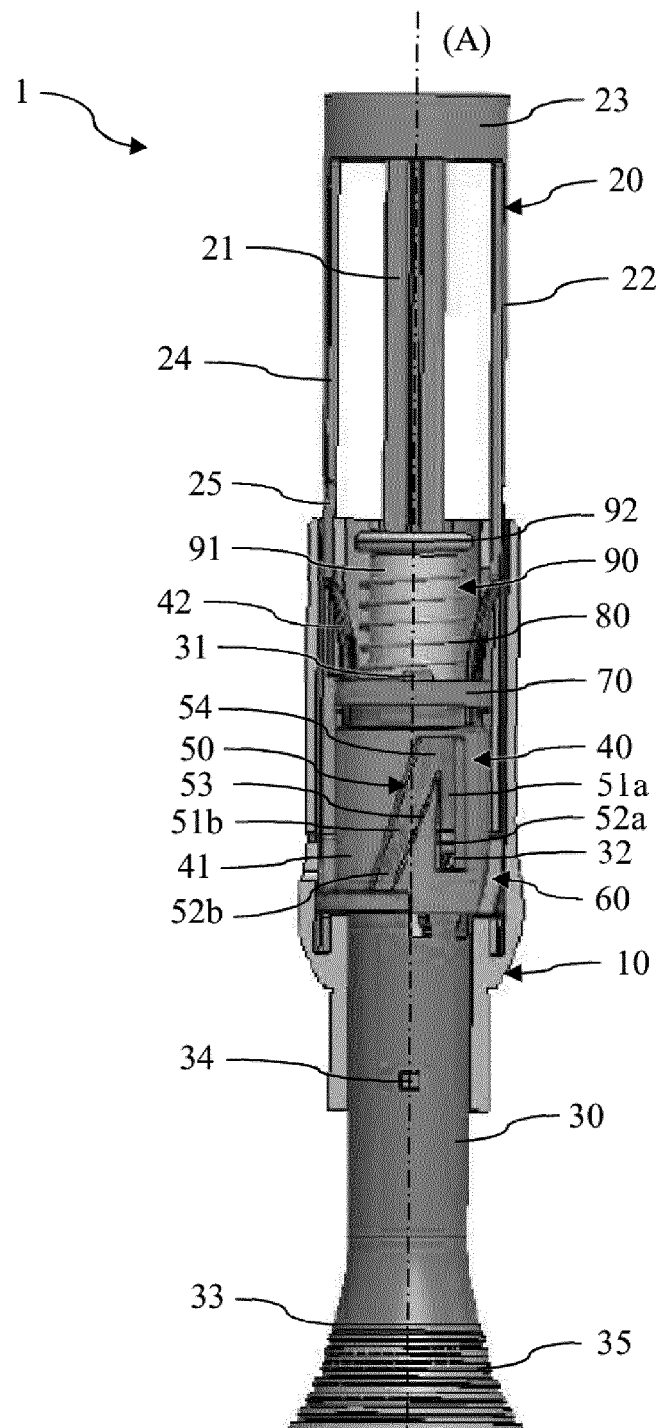
FIG. 2 is a side perspective view of the device illustrated in FIG. 1.
Figure 2A:
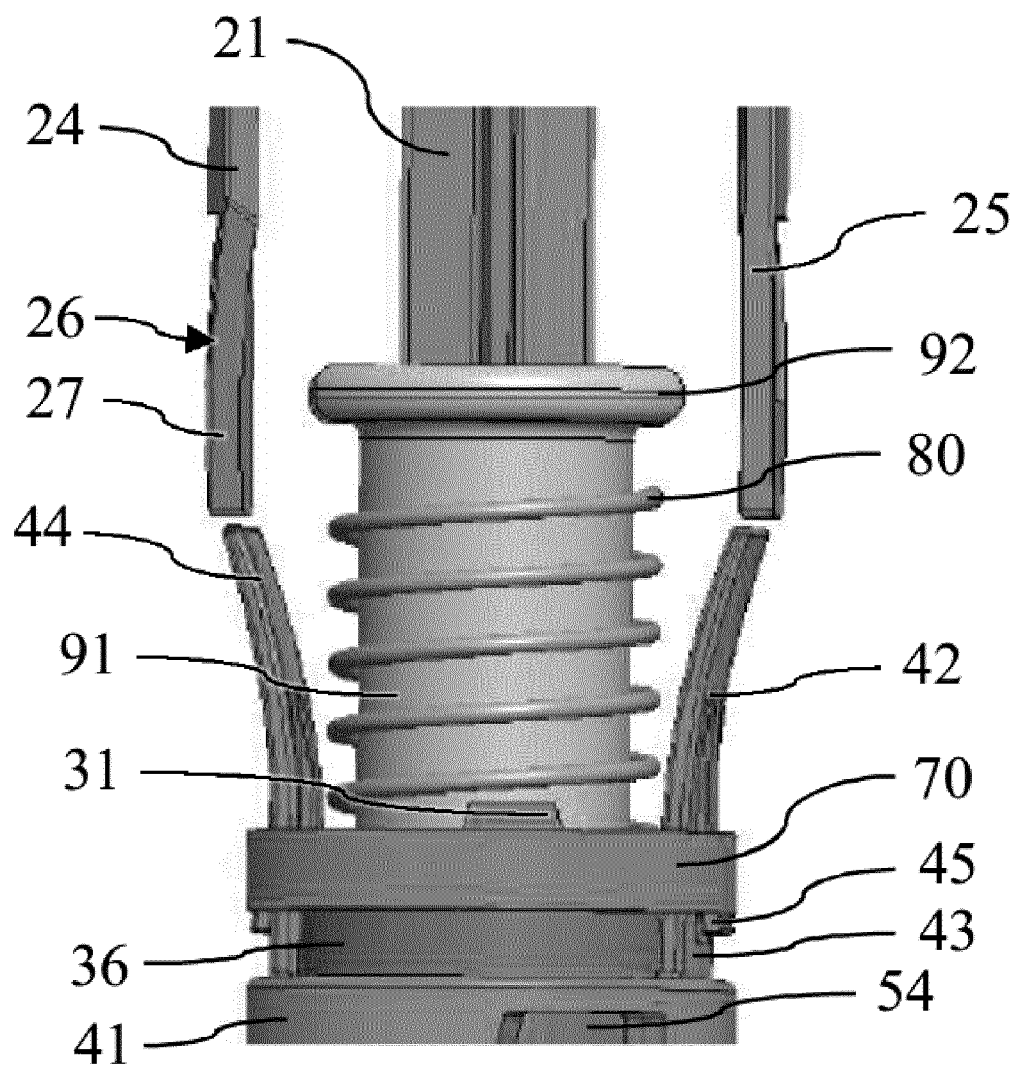
FIG. 2A is a is a close-up view of the device illustrated in FIG. 1.
Figure 3:
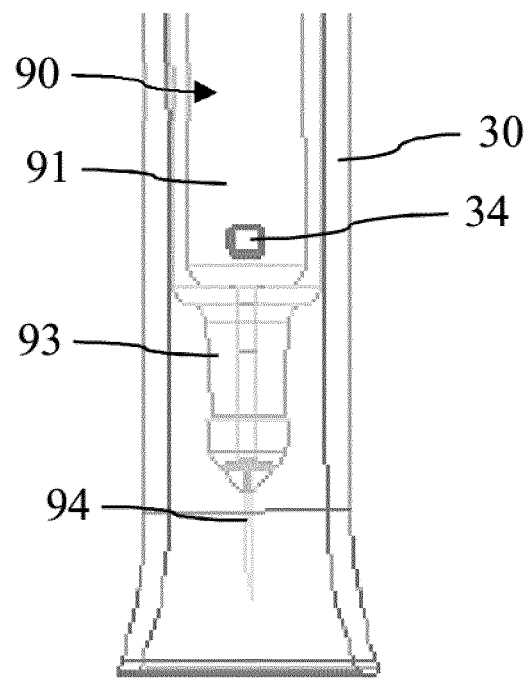
FIG. 3 is a side sectional view of the needle cover enclosing the medical container.
Figure 9:
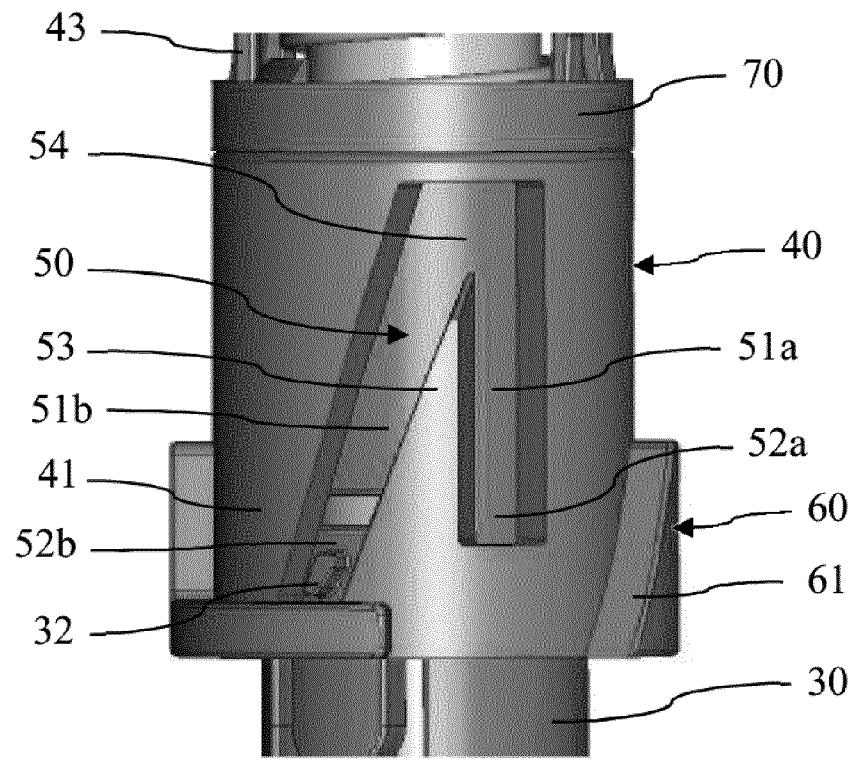
FIG. 9 is side perspective view of the ring in the device illustrated in FIG. 8.
Figure 10:
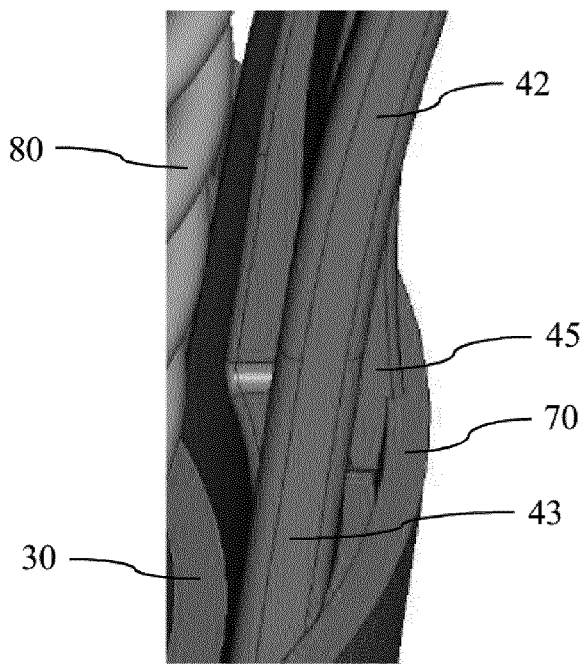
FIG. 10 is a perspective view of a portion of the ring illustrated in FIG. 9.
Figure 11:
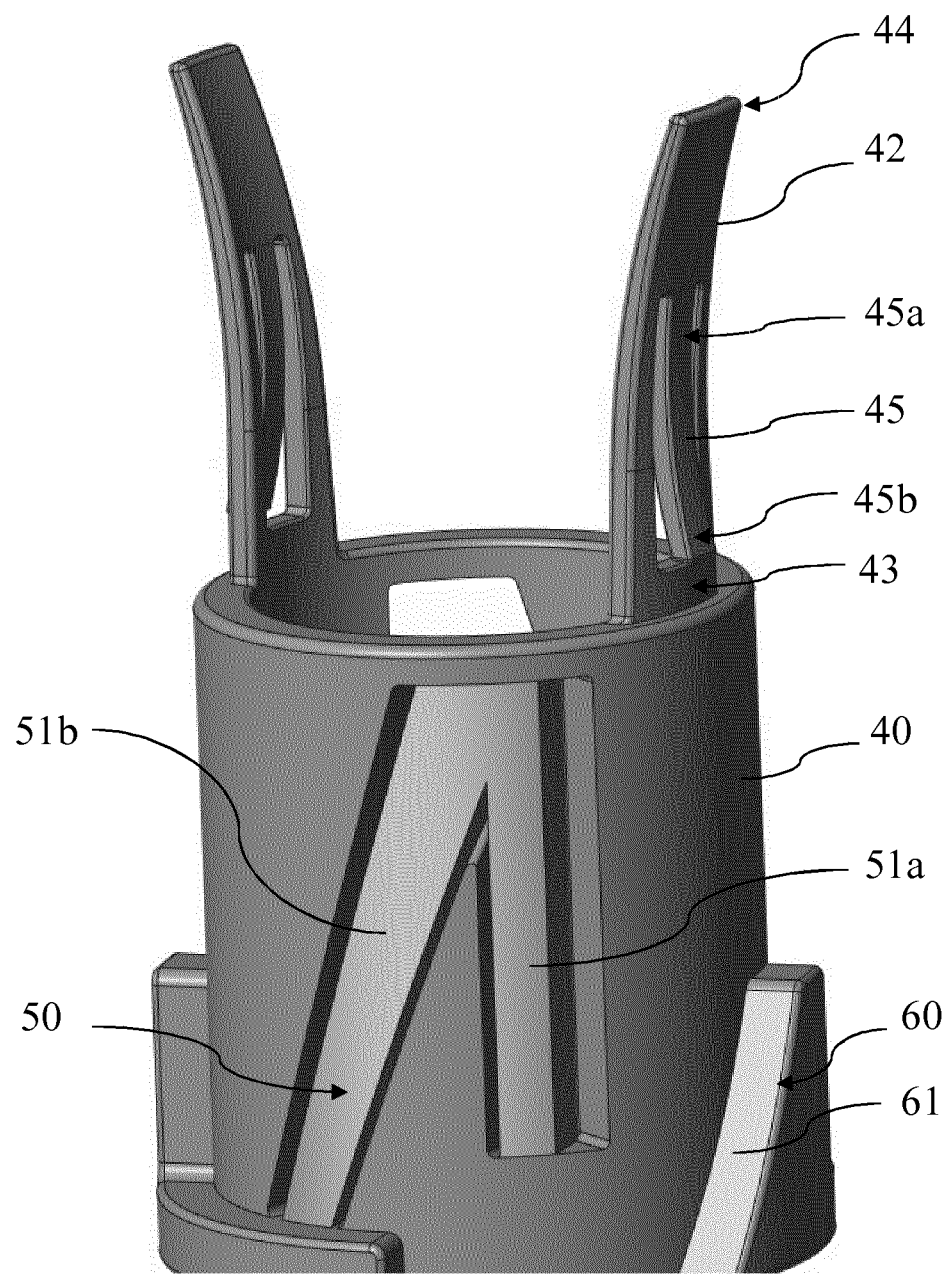
FIG. 11 is a perspective view of the ring in the device illustrated in FIG. 8.

To that purpose, according to one embodiment shown on FIGS. 1 to 11 the locking member 42 may comprise flexible legs as illustrated in FIGS. 2, 2A and 11, extending proximally from the body 41 of the ring 40. In the illustrated embodiment, the locking member 42 comprises two legs. However, it could comprise more than two legs or only one flexible leg protruding from the ring 40. The flexible legs are inclined. Each leg comprises a base 43 and a free end 44. When the legs are in rest position, the distance between the bases 43 of the two legs is less than the distance between the two free ends 44 of the legs. The legs can be deflected inwardly in order to decrease the distance between the free ends 44 of the legs.

More precisely, when the flexible legs 42 are in rest position, the free ends 44 of the legs abut against the outer plunger body 22 of the plunger, such that the plunger cannot move in the distal direction. When the flexible legs 42 are in rest position, the distance between the free ends of the flexible legs is equal to the transversal dimension of the outer plunger body 22, for example the diameter of the outer plunger body 22 when it has a cylindrical shape. When the flexible legs are deflected inwardly, the distance between the free ends of the flexible legs is less than the transversal dimension of the outer plunger body 22 such that the outer plunger body 22 of the plunger is free to move distally. In this embodiment, the locking member transitions from the locking position to the unlocking position thanks to elastic deformation of the legs.

Figure 4:
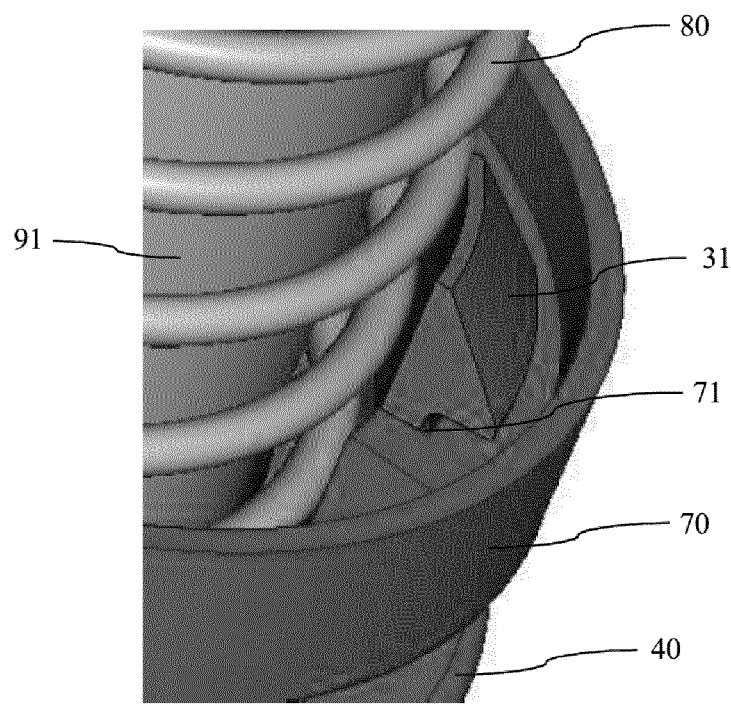
FIG. 4 is a perspective view of the proximal end of the needle cover with a locking ring mounted thereon.

As represented on FIGS. 1 to 11, the needle cover 30 may further comprise a locking ring 70 at its proximal end 36. The locking ring 70 may be mounted on the needle cover via fixing means so as to be fixed at least axially, preferably also fixed rotatably, relative to the needle cover 30. The fixing means preferably include a clipping system wherein a clip 31 extending from the proximal end of the needle cover 30 is adapted to be inserted in a corresponding recess 71 of the locking ring 70, as illustrated in FIG. 4. Moreover, the locking ring 70 is positioned around the bases 43 of the flexible legs in the storage position shown in FIGS. 2 and 2A. The locking ring 70 has an interior diameter superior to the distance between the bases 43 of the flexible legs. The locking ring 70 has an interior diameter inferior to the distance between the free ends 44 of the flexible legs in rest position. When the locking ring 70 moves proximally from the bases of the flexible legs to their free ends, the flexible legs are deflected inwardly.

Figures 12A, 12B, 12C, 12D:
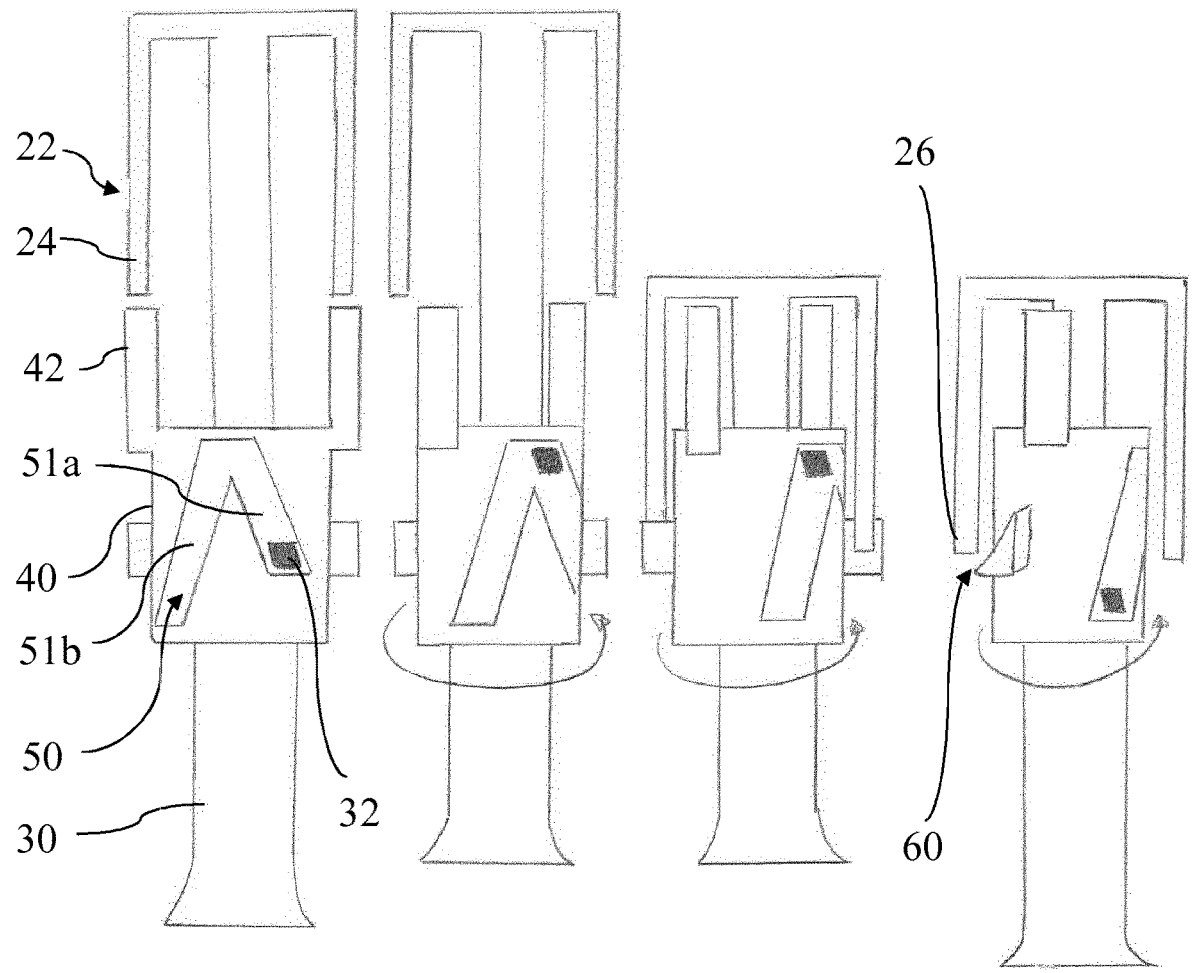
FIGS. 12A to 12D represent another embodiment of the invention.

Alternatively, as represented on FIGS. 12A to 12D, the locking member 42 could comprise legs abutting against the outer plunger body 22 of the plunger. The legs are preferably rigid. In storage position (see FIG. 12A), the legs 42 of the ring 40 abut against the arms 24 of the outer plunger body 22. The plunger cannot move distally as long as the legs 42 of the ring 40 are aligned with the arms 24 of the plunger. When the needle cover is retracted in injection position (see FIG. 12b), the ring 40 is rotated so that the legs 42 of the ring 40 are not aligned anymore with the arms 24 of the outer plunger body 22. When the needle cover is retracted in injection position, the legs 42 of the ring 40 do not abut anymore against the arms 24 of the outer plunger body 22 so that the plunger is free to move distally. In this embodiment, the locking member 42 transitions from the locking position to the unlocking position thanks to rotation of the legs. The rotation of the locking member is triggered by the proximal movement of the needle cover. FIG. 12C illustrates the configuration of the device at the end of injection. FIG. 12D illustrates the configuration of the device with the needle cover in safety position.

To that purpose, in the embodiment of FIGS. 12A-12D, the ring 40 may comprise a groove 50. The needle cover 30 may comprise a lug 32 received in the groove 50. Alternatively, the needle cover 30 could comprise a groove and the ring 40 could comprise a lug. The groove 50 comprises a first branch 51a and a second branch 51b. The lug 32 moves into the first branch 51a when the needle cover moves from the storage position to the injection position. The lug 32 moves into the second branch 51b when the needle cover 30 moves from the injection position to the safety position. The first branch 51a is angled so that the ring 40 rotates relative to the plunger 20 when the needle cover 30 moves proximally from the storage position to the injection position. When the needle cover is retracted proximally from the storage position to the injection position, the ring 40 rotates so that the legs 42 of the ring 40 are not aligned anymore with the arms 24 of the outer plunger body 22. The plunger may then move distally.

The injection device of all represented embodiments is configured so that the needle cover cannot move in safety position as long as the plunger has not moved distally to a triggering position. Said triggering position is reached once the plunger has moved distally a distance at least equal to a given threshold distance. In other words, the injection device is configured so that the distal movement of the plunger triggers the transition of the needle cover from the injection position to the safety position. This transition of the needle cover from the injection position to the safety position preferably occurs when the plunger is close of its most distal position and more preferably when the plunger has reached its most distal position such that the needle cover is allowed to move in the safety position only once the full dose of drug has been injection.

To that purpose, the injection device preferably comprises a groove 50 and a lug 32 configured to move in the groove 50. The groove 50 may be on the body 10, on the needle cover 30 or on the ring 40 when the injection device has a ring. The lug 32 may be on the needle cover 30, on the body 10 or on the ring 40 when the injection device has a ring.

The groove 50 comprises a first branch 51a and a second branch 51b. The first branch 51a and the second branch 51b are preferably inclined one relative to the other. The lug 32 is in the first branch 51a when the needle cover 30 moves from the storage position to the injection position and when the needle cover 30 moves from the injection position to the storage position again if this movement happens.

The lug 32 is in the second branch 51b when the needle cover 30 moves from the injection position to the safety position. The lug 32 must transition from the first branch 51a to the second branch 51b to allow the needle cover to move in safety position. In other words, once the lug 32 is in the second branch 51b, the needle cover 30 is allowed to move from the injection position to the safety position.

To that purpose, the plunger 20 preferably comprises a triggering member 26 configured to transition the lug 32 from the first branch 51a to the second branch 51b when the plunger 20 moves distally.

According to different embodiments:

the triggering member 26 may be configured to displace the groove 50 relative to the lug 32 so that the lug 32 passes from the first branch 51a to the second branch 51b. In this embodiment, the groove 26 is preferably formed in a part that can be rotated by the triggering member 26 of the plunger so that the lug 32 moves from the first branch 51a to the second branch 51b; or the triggering member 26 may be configured to move the lug 32 relative to the groove 50 so that the lug 32 passes from the first branch 51a to the second branch 51b. In this case, the lug 32 is preferably located on a flexible arm that can be deflected by the triggering member 26 of the plunger so that the lug 32 moves from the first branch 51a to the second branch 51b.

Different embodiments will be more precisely described with reference to the figures.

According to the embodiment represented on FIGS. 1 to 11, the groove 50 is provided in the body 41 of the ring 40, adapted to receive a first lug 32 extending outwardly from the wall of the needle cover 30. The groove 50 includes two branches, wherein a first branch 51a extends axially in the ring 40, and a second branch 51b extends obliquely relative to the first branch. The two branches 51a, 51b are partially separated by a portion 53 of the body 41 of the ring 40, and meet proximally at a junction 54. The distal end 52b of the second branch preferably is in a more distal position than the distal end 52a of the first branch.

The ring 40 is provided with cam members 60 that define inclined surfaces 61. The triggering member 26 of the plunger is preferably located at an end of the outer plunger body 22. The triggering member 26 is preferably an inclined surface configured to rotate the ring 40 when it is translated on the cam member 60 of the ring.

In the following, the functioning of the device of FIGS. 1 to 11 will be detailed in reference to the embodiment of the device described above. It has to be known that other embodiments of the device would result in a similar functioning, notwithstanding their structural differences.

FIG. 2 shows the injection device 1 before use.

In this configuration, the needle cover 30 is in the storage position and covers the needle 94. The plunger 20 is maintained in the proximal position by the ring 40, and more precisely by the locking member 42 of the ring that abuts against the outer plunger body 22 of the plunger 20. Indeed, in storage position, the locking ring 70 is positioned around the base of the flexible legs 42, such that the flexible legs 42 are in rest position. As a matter of fact, when the locking ring 70 is positioned around the bases of the flexible legs, the flexible legs are not deflected by the locking ring 70. Hence, the free end 44 of the flexible legs is aligned with the distal end 25 of the outer plunger body. The flexible legs 42 thus act as an axial mechanical stop for the outer plunger body that prevents the plunger 20 from moving in a distal direction. As a matter of fact, no injection can take place as long as the needle cover is not retracted. In other words, no injection can occur as long as the needle is not pricked into the skin.

In the storage position, the lug 32 of the needle cover 30 is positioned at the distal end 52a of the first branch and abuts the body 41 of the ring.

Figure 5:
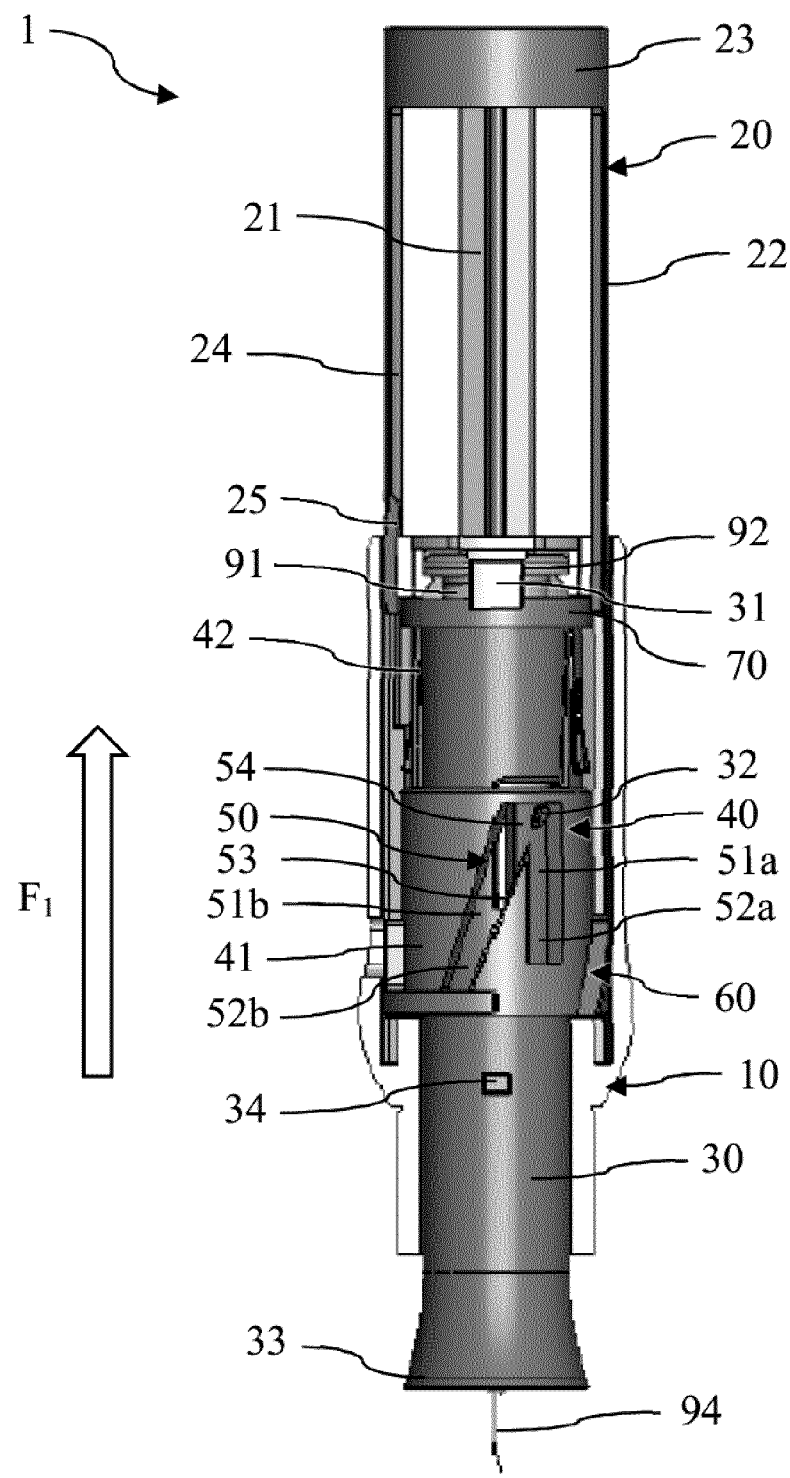
FIG. 5 is a side perspective view of the device during pricking of the skin of the user or patient, wherein the needle cover is in the injection position.

In reference to FIG. 5, for using the device, the user first removes the cap 35, when present, from the distal end 33 of the needle cover, which advantageously removes the needle shield or the rigid needle shield of the medical container 90 at the same time.

Then, the user positions the injection device on the skin so as to put the distal end 33 of the needle cover 30 into contact with the skin. The user either directly presses the body 10 of the device 1 towards its skin or he may push on the plunger 20. As the plunger is axially locked with respect to the body 10 as long as the needle cover 30 is not retracted, when the user presses the plunger 20 towards the skin, the set plunger-body-ring-medical container is pressed towards the skin. The needle cover 30 is then retracted inside the body 10. The needle is then pricked into the skin. More precisely, the needle cover moves in the proximal direction according to the arrow $F_1$ relative to the body 10. When the needle cover 30 moves proximally with respect to the body 10, the locking ring 70 that is fixed to the needle cover 30 also moves proximally with respect to the body 10 and then with respect to the ring 40.

The movement of the needle cover 30 in the distal direction causes the locking ring 70 to slide accordingly on and along the flexible legs 42, thereby deflecting each flexible leg inwardly towards the axis (A). The free ends 44 of the flexible legs is no more aligned with the outer plunger body 22, and the plunger 20 is thus allowed to move with respect to the body 10 in a distal direction.

When the needle cover 30 moves proximally with respect to the body 10, the spring 80 is compressed between a transversal surface S1 of the body and a transversal surface of the needle cover or between a flange of the medical container and a transversal surface of the needle cover. The needle cover 30 remains in the injection position as long as the user keeps pressing the needle cover against the skin.

Figure 6:
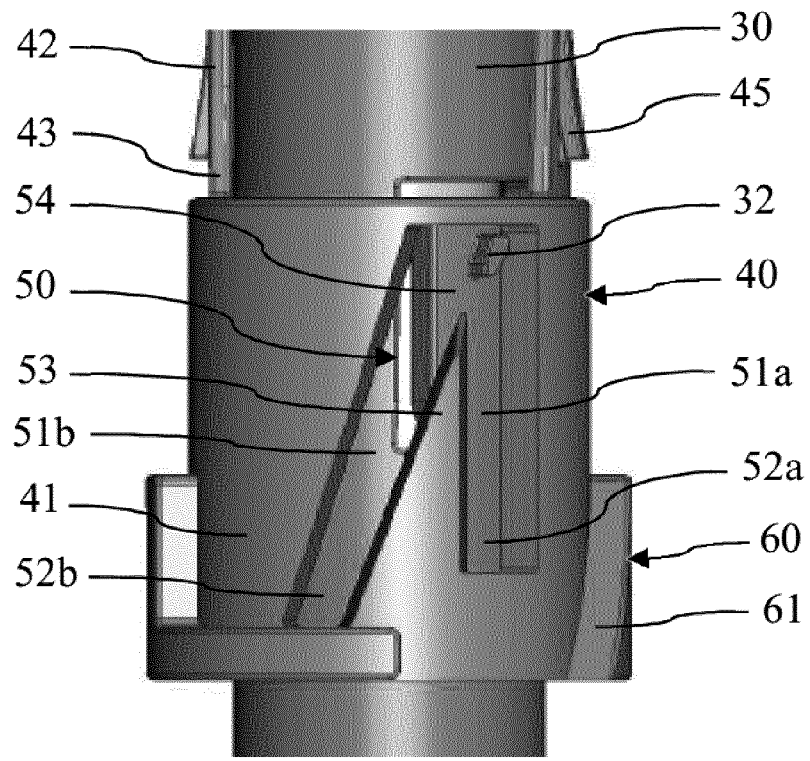
FIG. 6 is a side perspective view of the ring in the device illustrated in FIG. 5.

At the same time, in reference to FIG. 6, the first lug 32 of the needle cover 30 moves along the first branch 51a of the ring 40, from the distal end 52a of the first branch to the junction 54. As long as the lug 32 remains in the first branch 51a, the needle cover 30 cannot be positioned in safety position. The needle cover 30 can only be moved between the storage position and the injection position. This allows a user to prick the needle in different sites of the patient's body if needed without locking the needle cover in safety position.

According to a preferred embodiment, as illustrated in FIG. 5, after the needle cover has travelled a certain distance in the injection position, a second lug 34 provided in the needle cover 30 abuts the distal end of the ring 40, thus acting as an axial mechanical stop that prevents the needle cover from moving further proximally. The first lug 32 may itself act as a mechanical stop of the needle cover 30, making the second lug 34 optional, although it is not the case in FIG. 5.

As the plunger 20 is free to move in a distal direction, the user may proceed to the injection. In order to do so, the user presses the proximal end 23 of the plunger in the distal direction. This causes the central plunger rod 21 to slide inside the medical container 90 and to push the stopper so as to expel the composition from the needle 94 into the body of the patient.

At the same time, the outer plunger body 22 slides in a distal direction relative to the body 10 and the ring 40, and the cam members 26 of the outer plunger body 22 interact with the cam member 60 of the ring 40. In more details, when the plunger reaches a triggering distal position, i.e. when the inclined surfaces 27 of the outer plunger body 22 slide on and along the inclined surfaces 61 of the ring 40, the ring 40 to rotate about the axis (A) relative to the needle cover 30.

Figure 7:
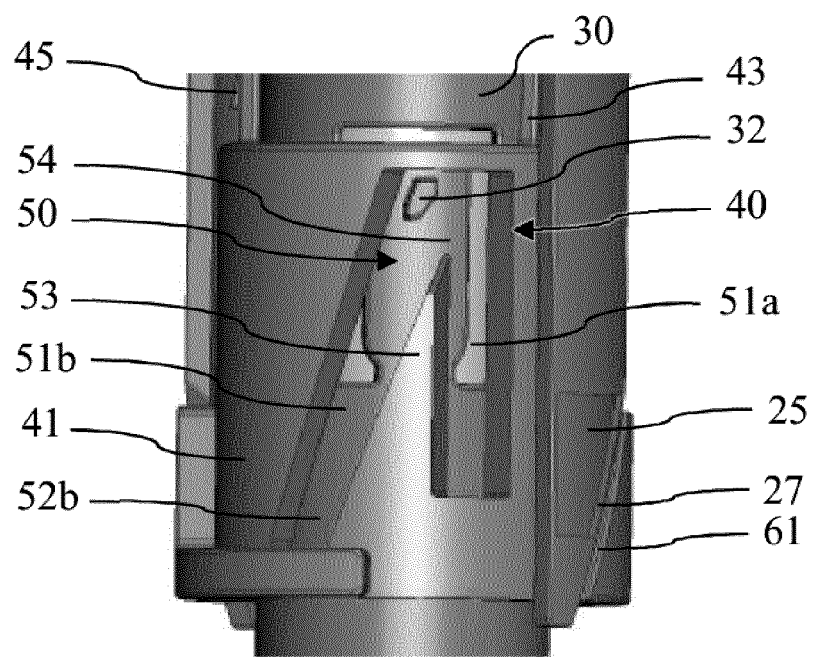
FIG. 7 is a side perspective view of the ring in the device after injection of the composition.

In reference to FIG. 7, the rotation of the ring 40 causes the first lug 32 to engage the second branch 51b of the groove 50. The rotation of the ring 40 preferably occurs only when the plunger has reached its most distal position so that the needle cover cannot be locked in safety position as long as the injection is not completed.

Figure 8:
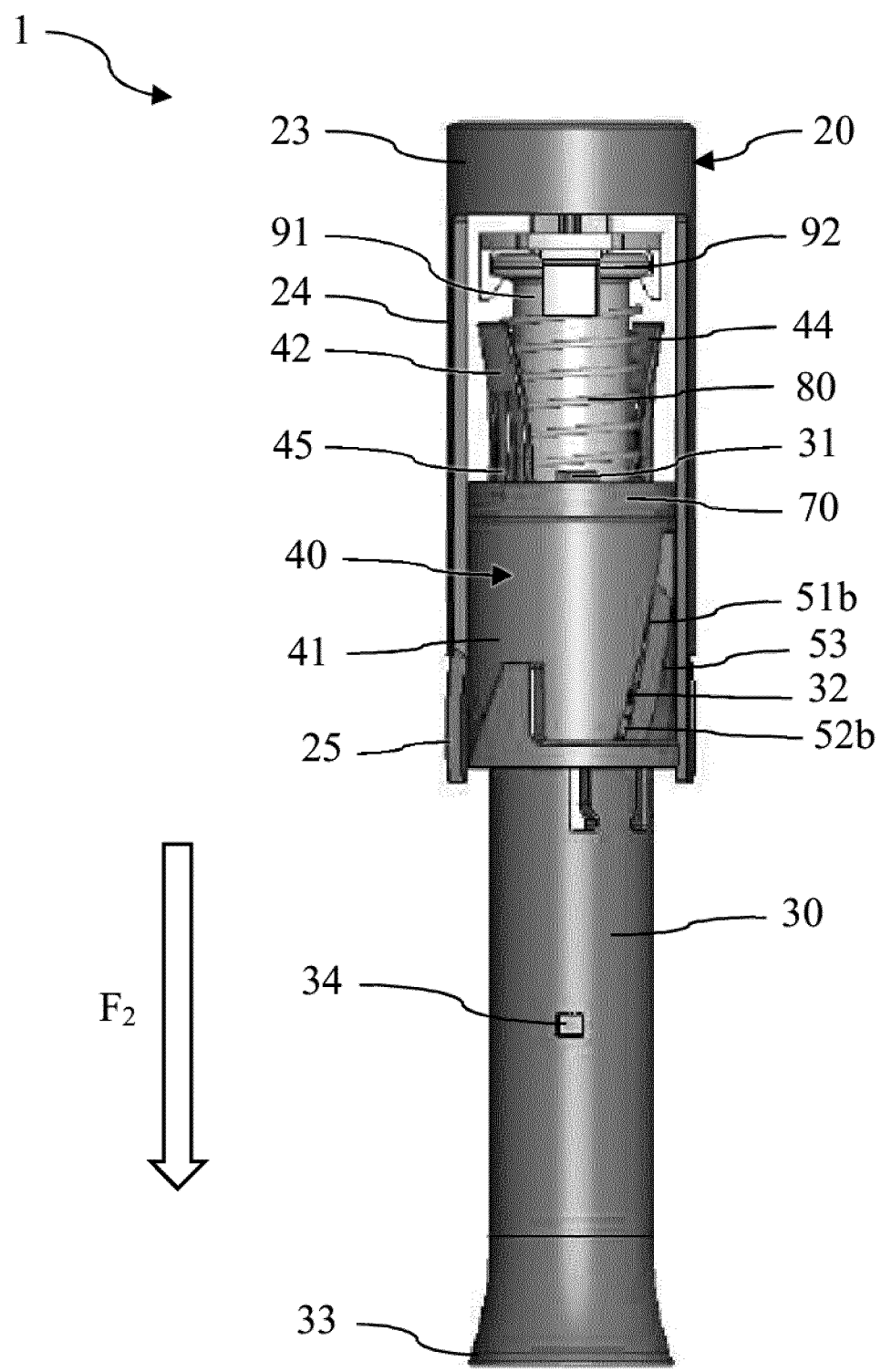
FIG. 8 is a side perspective view of the device after injection of the composition, wherein the needle cover is in the safety position.

In reference to FIG. 8, at the end of the injection, the user removes the device from the skin of the patient. The needle cover 30 is no more pressed against the skin, and thus moves back in a distal direction with the spring force of the spring member 80 which releases, to the safety position, as illustrated by the arrow $F_2$. By doing so, as illustrated in FIG. 9, the first lug 32 moves along with the needle cover 30, along the second branch 51b, from the junction 54 to the distal end 52b of the second branch. Preferably, the first lug 32 abuts the body 41 of the ring at the distal end 52b of the second branch. In that manner, the lug 32 acts as a mechanical stop that prevents the needle cover 30 from moving further distally.

According to the embodiment of FIGS. 1 to 11, as the distal end 52b of the second branch is more distal than the distal end 52a of the first branch, the position of the needle cover 30 in the safety position is more distal than that in the storage position.

In the safety position, the needle cover 30 covers the needle 94.

The injection device further comprises locking means configured to permanently lock the needle cover 30 in safety position.

The locking means preferably comprise at least one tab 45 and preferably two tabs 45. Each tab is configured to abut against a shoulder once the needle cover is in safety position in order to lock the needle cover in safety position.

In the embodiment of FIGS. 1 to 11, each tab 45 is a flexible tab 45. Each flexible tab 45 is cut in one of the flexible legs 42. Each flexible tab 45 has a base 45a and a free end 45b. The free end 45b of the flexible tab 45 is located distally from the base 45a of the flexible tab.

In reference to FIG. 10, the movement of the needle cover 30 in the distal direction causes the locking ring 70 to slide back on and along the flexible tabs 45. During this movement of the locking ring 70, the flexible tabs flex inwardly. When the locking ring 70 slides under the free end 45b of the flexible tabs 45, the flexible tabs 45 return in a position wherein they project outwardly away from the axis (A). The flexible tabs 45 abut against a stop surface of the locking ring 70 such that the locking ring 70 cannot move proximally. The flexible tabs 45 act as an axial mechanical stop that prevents the locking ring 70, and thus the needle cover 30, from moving in the proximal direction.

Therefore, when the device is in the safety position, the needle cover 30 covers the needle 94 thereby preventing any physical contact between a person and the needle, and is maintained in such safety position. The needle cover 30 cannot be moved axially relative to the body 10, and in particular, cannot be disassembled from said body, making the device unable to be further used.

The outer plunger body 22 may also be provided with a color indicator configured to be aligned with a window W of the body at the end of injection in order to indicate to a user the end of injection. For example, the color indicator may be placed on the end members 26 of the outer plunger body. At the end of injection, the color indicator is visible through the window W of the body.

Of course the invention is not limited to the embodiments described in the present description.

For example, the groove could present other shapes than those represented on FIGS. 1 to 11. For example, the groove 50 could present two symmetric branches 51*a*, 51*b* as represented on FIG. 12A to 12D. By "symmetric" is meant here that both branches are inclined with substantially the same angle relative to the distal-proximal direction; as described above, the branches may differ in length, in particular such that the distal end of branch 51*b* is located in a more distal position than the distal end of branch 51*a*.

Besides, the locking member 42 could be rigid instead of being flexible as described with reference to FIGS. 12A to 12B.

Figures 13A, 13B:
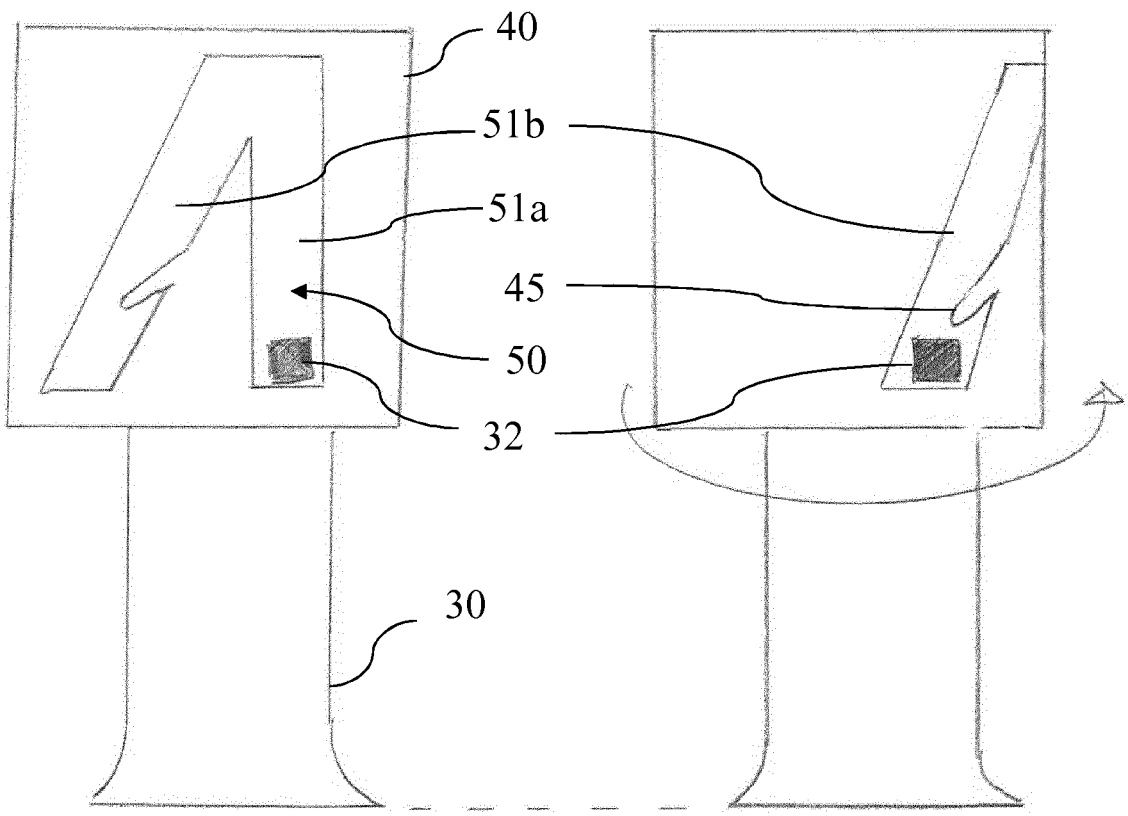
FIGS. 13A to 13B represent another embodiment of the invention.
Figures 14A, 14B, 14C, 14D:
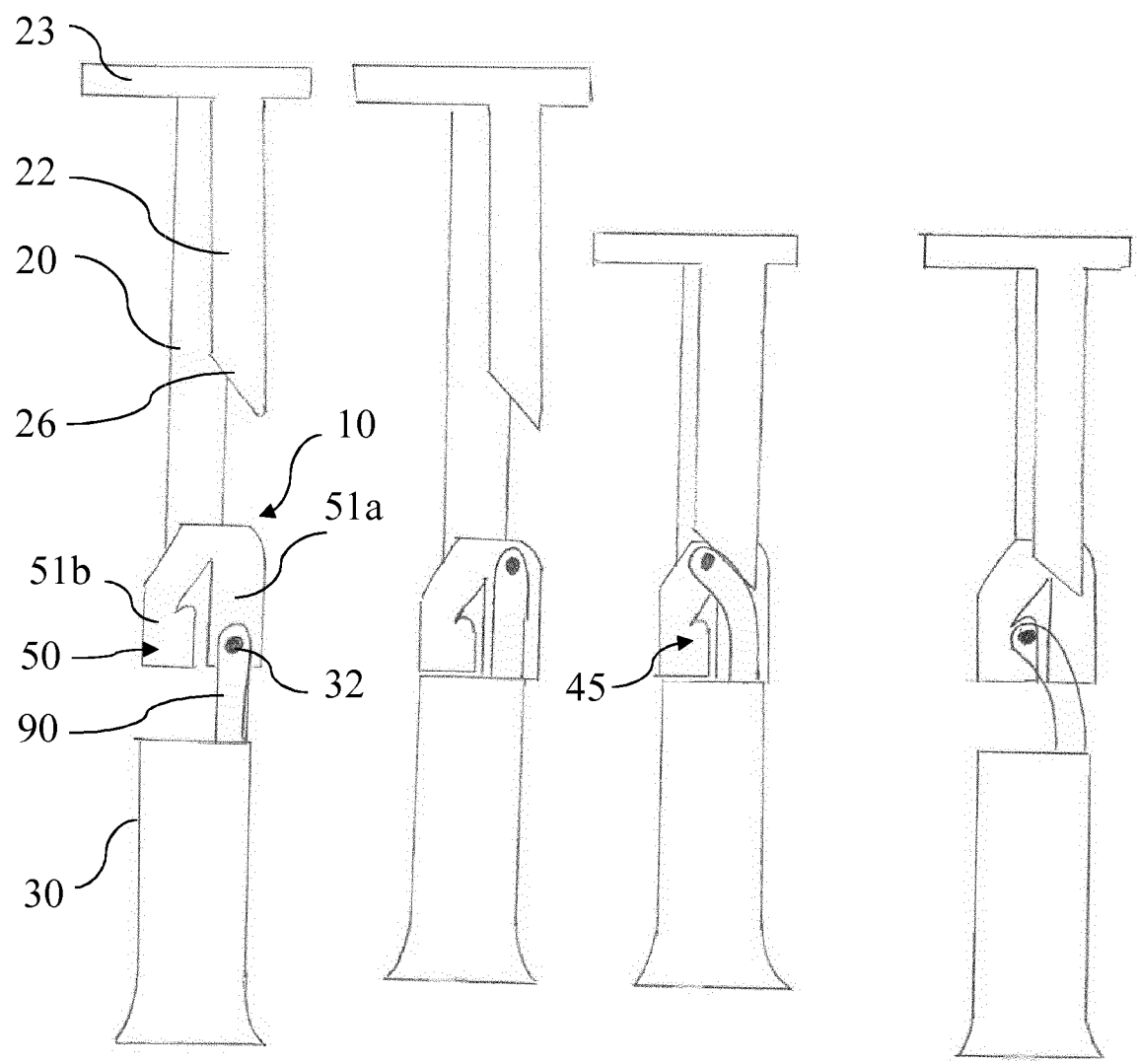
FIGS. 14A to 14D represent another embodiment of the invention.

Besides, the locking means 45 could be located on other parts of the ring 40 or on the needle cover 30 or even on the body 10. For example, as represented on FIGS. 13A and 13B, the locking means 45 could be a deflectable tab located in the groove 50 such that the deflectable tab is deflected by the lug 32 when the needle cover moves toward the safety position. The deflectable tab 45 is configured to be deflectable when the needle cover moves distally from the injection position to the safety position but not once the needle cover is in safety position in order to permanently lock the needle cover in safety position. FIG. 13A represents the configuration of the device in storage position. FIG. 13B represents the configuration of the device in safety position.

Alternatively, the locking means 45 could comprise flexible tabs located on the needle cover and configured to abut against a shoulder of the body once the needle cover is in safety position, or the locking means could comprise flexible tabs located on the body and configured to abut against a shoulder of the needle cover once the needle cover is in safety position.

Alternatively, the locking means could comprise a section of the groove 50 configured to prevent proximal movement of the lug once the lug is engaged in this section of the second branch of the groove.

Besides, instead of having a rotatable ring 40, the medical injection device according to the invention could comprise a flexible arm 90 extending proximally from the needle cover 30, the lug 32 protruding from the flexible arm 90, as represented on FIGS. 14A to 14D. In this embodiment, the groove 50 is located on the body 10 and the lug 32 is located on a flexible arm 90 protruding proximally from the needle cover 30. The triggering member 26 of the plunger is an inclined surface at the end of the outer plunger body 22. The outer plunger body 22 could be cylindrical or it could be an arm protruding from the proximal end 23 of the plunger. The triggering member 26 of the plunger is configured to push the lug 32 and to deflect the flexible arm 90 so that the lug 32 moves from the first branch 51*a* to the second branch 51*b* when the plunger moves distally. More precisely, once the plunger has moved toward a triggering distal point represented on FIG. 14C, the triggering member 26 of the plunger laterally deflect the lug 32 and the flexible arm until the flexible arm 90 is in the second branch 51*b*. The needle cover may then be pushed by the spring 80 from the injection position to the safety position (see FIG. 14D).

In the embodiment of FIGS. 14A to 14D, the locking means 45 comprise a section of the second branch 51*b* configured so that once the lug is in this section, it cannot move proximally. For example, said section may be located distally relative to a protrusion extending in the second branch to block the lug in the proximal direction.

The embodiments of the different figures could be combined according to all technically possible combinations.

The invention claimed is:

1. A medical injection device for supporting a medical container, said medical container comprising a barrel adapted to contain a composition and a needle extending from a distal end of the barrel, wherein the medical injection device comprises:
  a body configured to receive at least a part of the medical container;
  a plunger axially movable relative to the body along an axis of the body; and
  a needle cover movable relative to the body along the axis, the needle cover being configured to move successively between a storage position wherein the needle cover covers the needle, an injection position wherein the needle cover exposes at least partially the needle, and a safety position wherein the needle cover covers the needle and is prevented from moving back to the injection position,
  wherein the medical injection device further comprises:
  a groove comprising a first branch and a second branch extending from a junction with the first branch; and
  a lug connected to the needle cover, the needle cover being configured to move from the storage position to the injection position when the lug is in the first branch, the needle cover being configured to move from the injection position to the safety position when the lug is in the second branch,
  wherein when the needle cover is in the injection position, the plunger is configured to transition the lug from the first branch to the second branch when said plunger moves distally, and
  wherein the plunger is configured to rotate the groove when the plunger reaches a distal triggering position so that the lug moves from the first branch to the second branch.

2. The medical injection device of claim 1, wherein the plunger comprises an inclined surface configured to cause the groove to rotate relative to the plunger.

3. The medical injection device of claim 1, further comprising a ring in rotatable engagement with the needle cover, the groove being positioned on the ring, the lug being positioned on the needle cover.

4. The medical injection device of claim 1, wherein the groove has a V-shape having a summit located proximally.

5. The medical injection device of claim 1, further comprising a locking system configured to lock the needle cover in the safety position.

6. The medical injection device of claim 5, wherein the locking system comprises at least one flexible tab configured to be deflected when the needle cover moves from the injection position to the safety position, the at least one flexible tab being configured to prevent proximal movement of the needle cover when the needle cover is in the safety position.

7. The medical injection device of claim 6, wherein the needle cover comprises a stop surface arranged so that the flexible tab abuts against the stop surface when the needle cover is in the safety position.

8. The medical injection device of claim 1, wherein the second branch is longer than the first branch.

9. The medical injection device of claim 1, further comprising a ring cooperating with the needle cover to prevent any axial movement of the plunger when the needle cover is in the storage position, and to allow axial movement of the plunger in a distal direction to expel the composition contained in the barrel from the needle when the needle cover is in the injection position, wherein the ring comprises a locking member configured to form an abutment preventing any axial movement of the plunger in the distal direction when the needle cover is in the storage position, and be moveable so that the plunger is allowed to move axially in the distal direction when the needle cover is in the injection position.

10. The medical injection device of claim 9, wherein the locking member is a flexible member configured to form an abutment preventing any axial movement of the plunger in the distal direction when the needle cover is in the storage position, and be deflected inwardly so that the plunger is allowed to move axially in the distal direction when the needle cover is in the injection position.

11. The medical injection device of claim 10, wherein the flexible member comprises at least two flexible legs extending proximally from the ring and the needle cover comprises a locking ring cooperating with said legs such that, when the needle cover is in the storage position, the locking ring is located around a distal base of the legs and when the needle cover is moved to the injection position, the locking ring is caused to slide along the legs, thereby retracting each leg inwardly.

12. The medical injection device of claim 9, wherein the locking member comprises legs, the ring being configured to rotate relative to the plunger between a locking position wherein the legs abut the plunger so that the plunger cannot move distally and an unlocking position wherein the legs do not abut the plunger so that the plunger can move distally.

\* \* \* \* \*